US00PP09158P

United States Patent [19]

Walden

[11] Patent Number: Plant 9,158

[45] Date of Patent: Jun. 13, 1995

[54] MINIATURE ROSE PLANT NAMED 'JACPUPOT'

[75] Inventor: John K. Walden, Thousand Oaks, Calif.

[73] Assignee: Bear Creek Gardens, Inc., Medford, Oreg.

[21] Appl. No.: 293,712

[22] Filed: Aug. 22, 1994

[51] Int. Cl.[6] ..... A01H 5/00

[52] U.S. Cl. ..... Plt./7.1

[58] Field of Search ..... Plt. 7.1, 9, 10

*Primary Examiner*—Howard J. Locker

*Attorney, Agent, or Firm*—Klarquist Sparkman Campbell Leigh & Whinston

[57] ABSTRACT

A miniature rose plant having the unique combination of its flower color; thick, numerous petals (55 to 60); and compact growth habit.

1 Drawing Sheet

The present invention relates to a new and distinct variety of rose plant of the miniature class which was originated by me by crossing an unnamed seedling with the variety JACliang (U.S. Plant Pat. No. 8,402.

The primary objective of this breeding was to produce a new rose variety having the plant habit and blooming habit of the female parent combined with the color and higher petal number of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, compact growth habit;
2. High petal count;
3. Novel flower color;
4. Thick petal substance; and
5. Free development of basal shoots from bottom of plant providing occasional small clusters of flower.

Asexual reproduction of this new variety by softwood cuttings, as performed at Wasco and Somis, Calif., shows that the foregoing characteristics and all other features come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—An unnamed seedling.

*Pollen parent.*—JACliang (U.S. Plant Pat. No. 8,402).

Classification:

*Botanical.*—*Rosa hybrida.*

*Commercial.*—Miniature.

FLOWER

Observations made from specimens grown in a greenhouse environment at Somis, Calif. in June 1994.

Blooming habit: Recurrent.

Bud:

*Size.*—7/16 inch long when the petals start to unfurl.

*Form.*—The bud form is blunt topped.

*Color.*—When sepals first divide, bud color is Red-Purple Group 61B. When half blown, the upper and lower sides of the petals are Red-Purple Group 63A.

*Sepals.*—Color: Yellow-Green Group 144A. Surface texture: Smooth, lightly tomentose. There are three lightly appendaged sepals. There are two unappendaged sepals with hairy edges.

*Receptacle.*—Color: Yellow-Green Group 144A. Shape: Funnel. Size: Small ($\frac{1}{4}$ inch$\times$3/16 inch). Surface: Smooth.

*Peduncle.*—Length: Short. Surface: Smooth, glandular. Color: Yellow-Green Group 144A. Strength: Stiff, erect, slender.

Bloom:

*Size.*—Small. Average open size is $1\frac{1}{4}$ inches to $1\frac{1}{2}$ inches.

*Borne.*—Singly and several together, in flat to slightly rounded clusters of 3 to 5 occasionally.

*Stems.*—Short, normal. Average length is about 3 to 4 inches.

*Opening.*—Opens fully exposing stamens and pistils.

*Form.*—When first open: Flat. Permanence: Outer petal edges curl slightly.

*Petalage.*—Number of petals under normal conditions: 55 to 60.

*Color.*—The upper side of the petals is Red-Purple Group 63A near outer half of petal, 69B on inner quarter of petal. The reverse side of the petals is Red-Purple Group 63A. The color of the base of petals is Yellow-Green Group 150D. The major color on the upper side is Red-Purple Group 63A.

*Variegations.*—None.

*Discoloration.*—The general tonality at the end of the first day: No change. At the end of the third day, no change.

*Fragrance.*—None.

Petals:

*Texture.*—Thick, leathery.

*Shape.*—Pointed, deltoid.

*Form.*—Tips slightly recurved, edges slightly quilled.

*Arrangement.*—Imbricated, with a few petaloids in the center.

*Persistence.*—Drop off cleanly.

*Lastingness.*—On the plant: Very long (10 to 12 days).

Reproductive parts:

*Anthers.*—Size: Small. Quantity: Many. Color: Yellow. Arrangement: Regular around styles.

*Filaments.*—Color: White.

*Pollen.*—Color: Lemon yellow.

*Styles.*—Color: White.

*Stigmas.*—Color: Greenish white.

Form: Bush.

Growth: Vigorous, dwarf, upright, branching, compact, 5 to 6 inches tall, 6 inches wide.

Foliage: Number of leaflets on normal mid-stem leaves: 5, occasionally 7.

*Size.*—Small ($2\frac{1}{4}$ inches $\times$ $1\frac{1}{8}$ inches).

*Quantity.*—Normal.

*Color.*—New foliage: Greyed-Red Group 178A, changing rapidly to green, edged in reddish purple on margins. Old foliage: Green Group 139A.

Leaflets:

*Shape.*—Pointed oval.

*Texture.*—Upper side: Leathery.

*Edge.*—Serrated.

*Serration.*—Double, small.

*Petiole rachis.*—Color: Reddish.

*Petiole underside.*—With prickles.

*Stipules.*—Medium, serrated.

*Disease resistance.*—Susceptible to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short ($\frac{1}{8}$ inch to 3/16 inch), straight.

*Color when young.*—Transparent.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its flower color; thick, numerous petals (55 to 60), and compact growth habit.

* * * * *

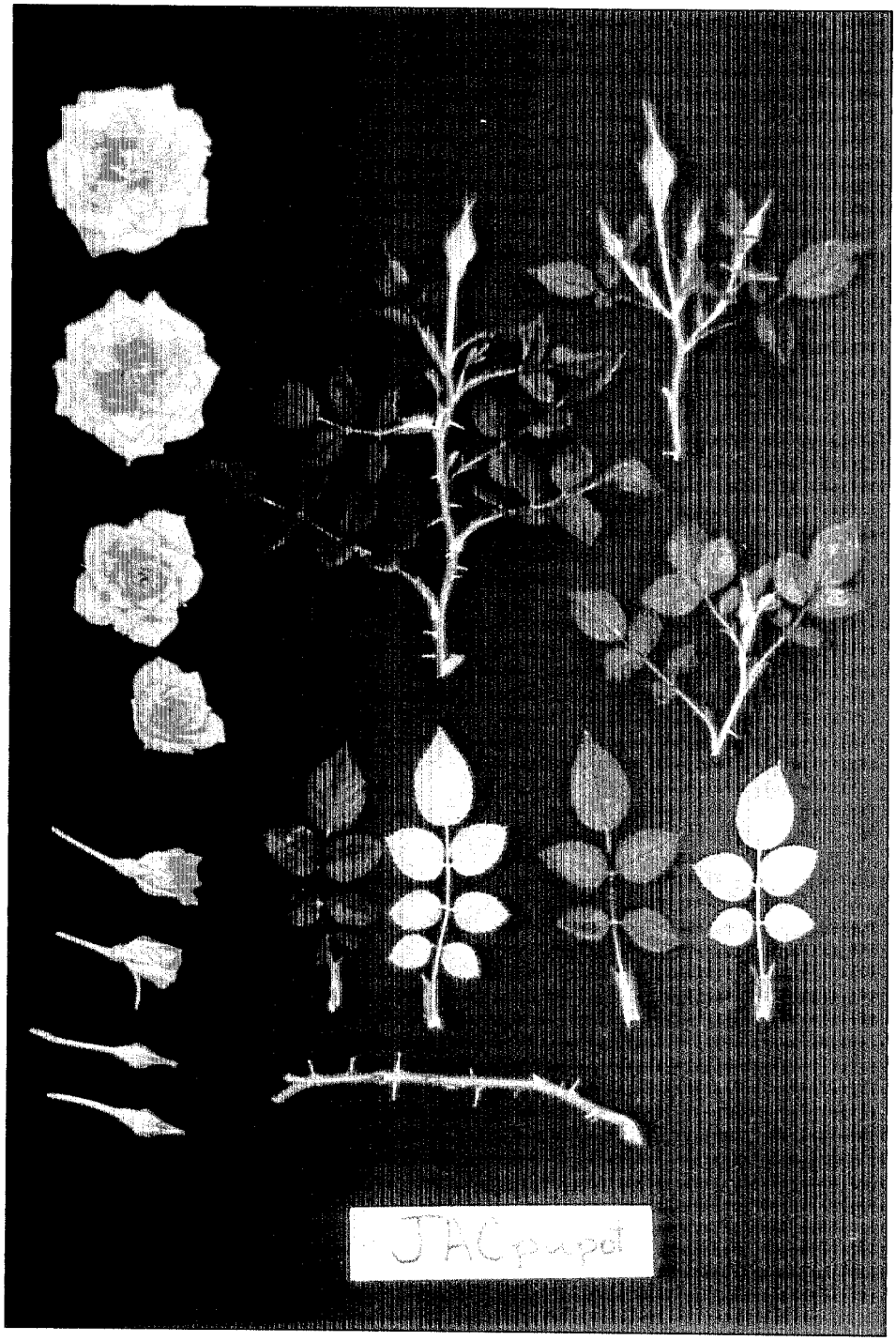
JHCpuzzel